US009240388B2

(12) United States Patent
Hirose

(10) Patent No.: US 9,240,388 B2
(45) Date of Patent: Jan. 19, 2016

(54) SEMICONDUCTOR MANUFACTURING DEVICE AND SEMICONDUCTOR MANUFACTURING METHOD

(71) Applicant: Kabushiki Kaisha Toshiba, Minato-ku (JP)

(72) Inventor: Osamu Hirose, Yokkaichi (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 14/475,726

(22) Filed: Sep. 3, 2014

(65) Prior Publication Data
US 2015/0255421 A1    Sep. 10, 2015

(30) Foreign Application Priority Data
Mar. 7, 2014   (JP) .................................. 2014-045032

(51) Int. Cl.
*H01L 23/00* (2006.01)
*G01N 3/02* (2006.01)
*G01N 19/08* (2006.01)

(52) U.S. Cl.
CPC *H01L 24/80* (2013.01); *G01N 3/02* (2013.01); *G01N 19/08* (2013.01)

(58) Field of Classification Search
CPC ................... H01L 2924/3512; G01N 21/9505; G01N 21/9501
See application file for complete search history.

(56) References Cited

U.S. PATENT DOCUMENTS

| 6,890,304 | B1 * | 5/2005 | Amano | A61B 5/02 600/500 |
| 8,224,062 | B2 | 7/2012 | Ohkura et al. | |
| 8,680,876 | B2 * | 3/2014 | Kadono | G06F 3/041 324/658 |
| 9,019,498 | B2 * | 4/2015 | Sakai | G01N 21/21 356/369 |
| 2010/0117483 | A1 * | 5/2010 | Tanaka | H03H 3/08 310/313 B |
| 2010/0186512 | A1 * | 7/2010 | Goto | G01N 29/075 73/632 |
| 2012/0262715 | A1 * | 10/2012 | Sakai | G01N 21/21 356/369 |

FOREIGN PATENT DOCUMENTS

| JP | 3241050 B2 | 12/2001 |
| JP | 2006-156978 A | 6/2006 |
| JP | 2008-096319 A | 4/2008 |
| JP | 2009-243913 A | 10/2009 |
| JP | 4906897 B2 | 3/2012 |
| JP | 4973062 B2 | 7/2012 |
| JP | 2014-154826 A | 8/2014 |

* cited by examiner

Primary Examiner — S. V. Clark
(74) Attorney, Agent, or Firm — Oblon, McClelland, Maier & Neustadt, L.L.P.

(57) ABSTRACT

According to one embodiment, a semiconductor manufacturing device includes a first stage, a second stage, a transfer unit, and a detector. The first stage corrects a position of the semiconductor chip. The second stage supports an object into which the semiconductor chip is to be installed. The transfer unit transfers the semiconductor chip picked up from the first stage to the second stage. The detector detects an elastic wave from the semiconductor chip. The detector is attached to at least one of the first stage and the second stage.

18 Claims, 4 Drawing Sheets

SEMICONDUCTOR MANUFACTURING DEVICE AND SEMICONDUCTOR MANUFACTURING METHOD

CROSS-REFERENCE TO RELATED APPLICATION

This application is based upon and claims the benefit of priority from Japanese Patent Application No. 2014-045032, filed on Mar. 7, 2014; the entire contents of all of which are incorporated herein by reference.

FIELD

Embodiments described herein relate generally to a semiconductor manufacturing device and a semiconductor manufacturing method.

BACKGROUND

In the recent years, aside from a capacity increase, size reduction and thinning of a semiconductor package are under progress for installing the same to a limited space. As the semiconductor package, there is a multilayer structure in which a plurality of semiconductor chips is laminated in one package. Under such a circumstance, due to a thickness of the semiconductor chips being very thin, a crack is easily generated in the semiconductor chips. The crack may occur by a load being accumulated at a portion with a foreign matter, in a case where a semiconductor chip is mounted on a stage on which the foreign matter is adhered.

The crack generated in the semiconductor chip is detected by an appearance observation inspection using a magnification observation and recognition camera, for example. For example, a method in which a surface of the semiconductor chip mounted on the stage is taken by the recognition camera, and image information obtained therefrom is processed is known. In this method, there is a case in which a contrast difference becomes small between the crack and a portion on a periphery thereof, when a resin layer is formed on the surface of the semiconductor chip. It becomes difficult to obtain an accurate inspection result by the determination on the crack becoming insufficient.

For example, a method in which infrared light is irradiated from a rear surface side of the semiconductor chip having the resin layer formed on its surface, and the crack is detected from a difference in reflected light is known. In this method, there is a case in which the contrast difference becomes small between the crack and the portion on the periphery thereof, when an adhering layer is formed on a rear surface of the semiconductor chip. It becomes difficult to obtain an accurate inspection result by the determination on the crack becoming insufficient. Further, a structure of the semiconductor manufacturing device becomes complicated by providing a facility to irradiate with the infrared light from the rear surface side.

In a case where the crack generated in the semiconductor chip is not detected before being packaged, and is determined as a defect for the first time upon an inspection of a finished product, that finished product is going to be dealt as a defective product. In this case, components other than the semiconductor chip in which the crack has occurred and manufacturing cost thereof are wasted. Further, a large number of defective products will be produced, due to the difficulty in specifying the cause of the crack.

DETAILED DESCRIPTION

In general, according to one embodiment, a semiconductor manufacturing device includes a first stage, a second stage, transfer unit, and a detector. The first stage has a semiconductor chip mounted thereon. The first stage corrects a position of the semiconductor chip. The second stage supports an object into which the semiconductor chip is to be installed. The transfer unit transfers the semiconductor chip picked up from the first stage to the second stage. The transfer unit mounts the semiconductor chip on the object. The detector detects an elastic wave from the semiconductor chip. The detector is attached to at least one of the first stage and the second stage.

Exemplary embodiments of a semiconductor manufacturing device and a semiconductor manufacturing method will be explained below in detail with reference to the accompanying drawings. The present invention is not limited to the following embodiments.

First Embodiment

Figure 1:
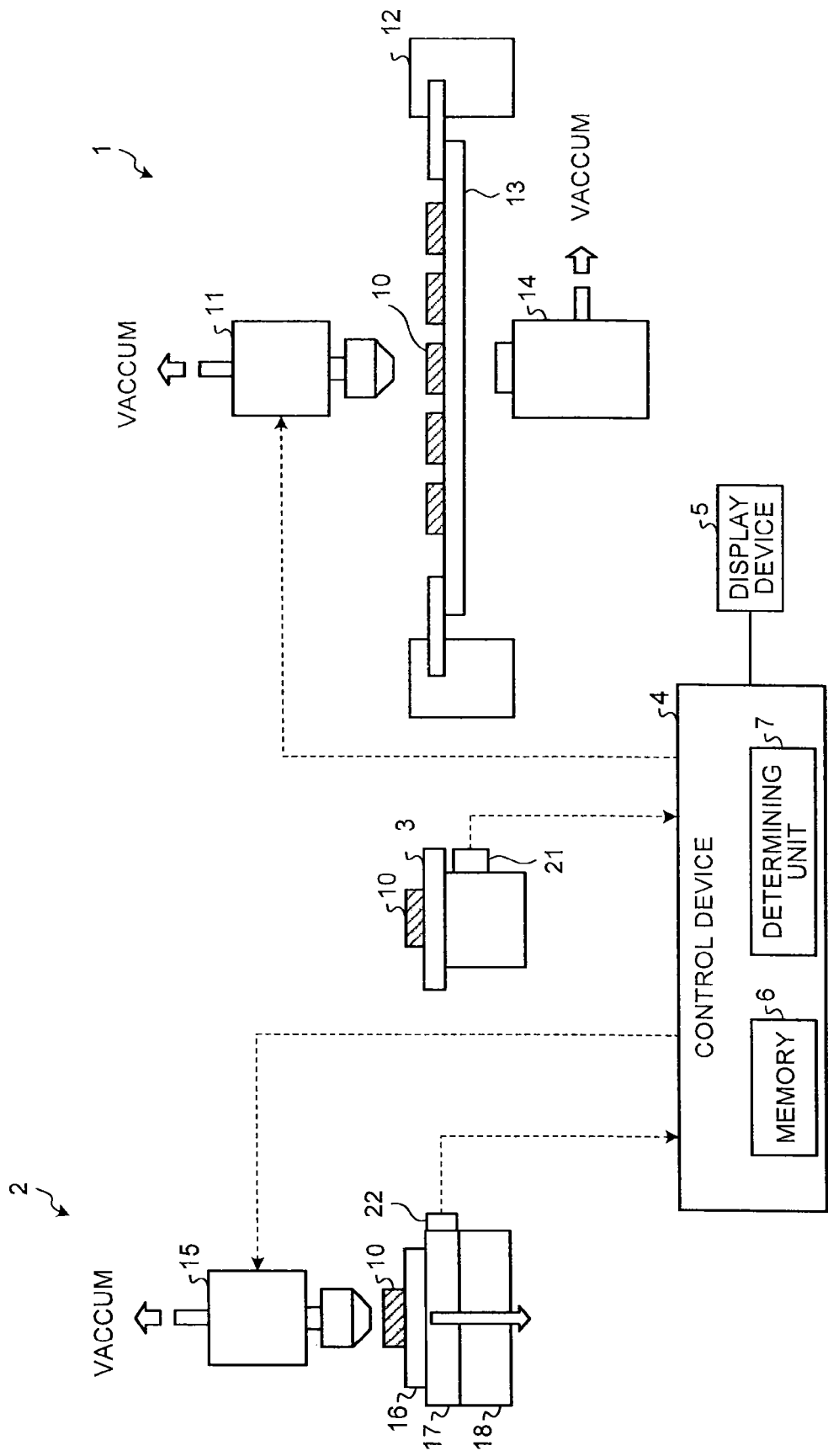
FIG. 1 is a diagram schematically illustrating a configuration of a semiconductor manufacturing device of a first embodiment.

FIG. 1 is a diagram schematically illustrating a configuration of a semiconductor manufacturing device of the first embodiment. The semiconductor manufacturing device includes a pick-up device 1, a die-bonding device 2, a preciser 3, a control device 4, and a display device 5. Notably, a "chip" and a "die" refer generally to those that are completely separated from a wafer, however, in the embodiment, wordings "chip", "die" and "wafer" will be used collectively for the sake of convenience, regardless of being before or after the separation. For example, there is a case where those divided into chip regions are referred to as a wafer, and there is a case where the chip regions before being completely separated are referred to as chips or dies.

The pick-up device 1 picks up separated semiconductor chips 10. The pick-up device 1 includes a die pick-up mechanism 11, a wafer stage 12, and a die eject mechanism 14. The pick-up device 1 is driven according to control signals from the control device 4.

The wafer stage 12 retains an outer peripheral portion of a dicing sheet 13. The separated semiconductor chips 10 are mounted on the dicing sheet 13. The dicing sheet 13 includes a resin-formed sheet base material and an adhesive layer. The sheet base material is configured of resin having elastic property, such as PVC (polyvinyl chloride), polyolefin, and the like. The adhesive layer is formed on one surface of the sheet base material. The semiconductor chips 10 are adhered on the adhesive layer. The adhesive layer is configured by using adhesives having a property by which adhering force is deteriorated by irradiation of ultraviolet (UV) light, for example.

The die eject mechanism 14 thrusts the semiconductor chips 10 upward from the rear surface side of the dicing sheet 13 by being driven in a vertical direction. The die eject mechanism 14 performs the thrusting operation on each of the semiconductor chips 10 while moving in a horizontal direction. The die eject mechanism 14 is connected to a vacuum pump (omitted from the drawings). Upon thrusting up the semiconductor chips 10, the die eject mechanism 14 sucks onto the rear surface of the dicing sheet 13 by using vacuuming by the vacuum pump.

The die pick-up mechanism 11 picks up the semiconductor chips 10 from the dicing sheet 13 by being driven in the vertical direction. The die pick-up mechanism 11 sucks and attaches the semiconductor chip 10 that is being thrust up by the die eject mechanism 14. The die pick-up mechanism 11 is connected to a vacuum pump (omitted from the drawings). The die pick-up mechanism 11 sucks onto the semiconductor chip 10 by using vacuuming by the vacuum pump.

The die pick-up mechanism 11 transfers the semiconductor chip 10 that had been picked up to the preciser 3 by a movement in a horizontal direction. The die pick-up mechanism 11 mounts the semiconductor chip 10 having been moved to the preciser 3 on the preciser 3.

The die pick-up mechanism 11 changes a position to pick up the semiconductor chip 10 in the horizontal direction to perform the picking-up operation on each of the semiconductor chips 10. The die pick-up mechanism 11 performs operations of picking up the respective semiconductor chips 10 on the dicing sheet 13 from the dicing sheet 13, and transferring to the preciser 3.

The semiconductor chip 10 transferred by the die pick-up mechanism 11 is mounted on the preciser 3 that is a first stage. The preciser 3 is a delivery carriage for delivering the semiconductor chip 10 between the pick-up device 1 and the die-bonding device 2. Further, the preciser 3 is also an alignment stage for correcting a position and an angle of the mounted semiconductor chip 10.

The semiconductor manufacturing device can perform the operation of the pick-up device 1 and the operation of the die-bonding device 2 independently by being provided with the preciser 3. The semiconductor manufacturing device can shorten processing time required for the pick-up and die-bonding of the semiconductor chips 10.

The detector 21 is attached to the preciser 3. The detector 21 detects an elastic wave from the semiconductor chip 10 mounted on the preciser 3. The detector 21 may be attached to any position on the preciser 3.

The die-bonding device 2 mounts the semiconductor chips 10 on an object 16. The object 16 is a member onto which the semiconductor chips 10 are mounted by the die-bonding device 2, for example, a lead frame, a wiring substrate, and the like. The die-bonding device 2 includes a die-bonding mechanism 15, and a die-bonding stage 17. The die-bonding device 2 is driven responsive to control signals from the control device 4.

The die-bonding stage 17 that is a second stage supports the object 16. The die-bonding stage 17 includes a heater 18 that is heating unit. The heater 18 heats the object 16 mounted on the die-bonding stage 17.

The die-bonding mechanism 15 that is a transfer unit picks up the semiconductor chip 10 from the preciser 3 by being driven in the vertical direction in a state of having been moved in the horizontal direction from the die-bonding stage 17 to the preciser 3. The die-bonding mechanism 15 sucks and attaches the semiconductor chip 10 on the preciser 3. The die-bonding mechanism 15 is connected to a vacuum pump (omitted from the drawings). The die-bonding mechanism 15 sucks onto the semiconductor chip 10 by using vacuuming by the vacuum pump.

The die-bonding mechanism 15 transfers the semiconductor chip 10 that had been picked up to the die-bonding stage 17 by a movement in the horizontal direction. Each time the semiconductor chip 10 is mounted on the preciser 3 by the die pick-up mechanism 11, the die-bonding mechanism 15 transfers the semiconductor chip 10 from the preciser 3 to the die-bonding stage 17. The die-bonding mechanism 15 mounts the semiconductor chip 10 having been moved to the die-bonding stage 17 on the object 16.

The detector 22 is attached to the die-bonding stage 17. The detector 22 detects an elastic wave from the semiconductor chip 10 mounted on the die-bonding stage 17. The detector 22 may be attached to any position on the die-bonding stage 17.

The detectors 21, 22 are for example piezoelectric elements (AE (Acoustic Emission) sensors). The detectors 21, 22 detect elastic energy that is emitted upon deformation and breakage of the semiconductor chips 10, and convert the detected elastic energy to electric signals. The elastic energy is energy of the elastic waves.

The elastic energy is generally discharged as an acoustic wave. The acoustic wave has radio frequency components primarily from several ten kHz to several MHz. The acoustic wave is generated accompanying deformation before a material reaches its breakage, or by generation of a crack. The semiconductor manufacturing device detects the acoustic wave by the detectors 21, 22, and thereby detects the deformation of the semiconductor chip 10 and the generation of a crack therein.

The detectors 21, 22 may include a filter for removing noise. The noise is an acoustic wave in a different frequency band from the acoustic wave generated by the cracking of the semiconductor chip 10. The filter may be configured either of hardware or software. Due to this, the semiconductor manufacturing device can accurately detect the generation of a crack in the semiconductor chip 10.

The control device 4 controls the drive of the pick-up device 1 and the die-bonding device 2. The control device 4 includes a memory 6 and a determining unit 7. The memory 6 retains various types of data for controlling the drive of the pick-up device 1 and the die-bonding device 2. The determining unit 7 that is determining unit determines the generation of a crack in the semiconductor chip 10 in accordance with the detection results of the elastic waves in the detectors 21, 22.

The semiconductor manufacturing device is not limited to those in which one control device 4 controls the drive of the pick-up device 1 and the die-bonding device 2. The semiconductor manufacturing device may provide a control device for each of the pick-up device 1 and the die-bonding device 2. In this case, the determining unit 7 for determining the generation of a crack according to the detection result of the elastic wave of the detector 21 may be provided in the control device that controls the pick-up device 1. The determining unit 7 for determining the generation of a crack according to the detection result of the elastic wave of the detector 22 may be provided in the control device that controls the die-bonding device 2.

The display device 5 that is display unit displays the determination result of the determining unit 7. Other than the above, the display device 5 may display various types of data related to the drive of the pick-up device 1 and the die-bonding device 2.

Foreign matters derived from a driving system of the pick-up device 1 and the die-bonding device 2, and foreign matters derived from materials such as silicon scraps, pieces of adhesive material and the like may adhere to the preciser 3. The silicon scraps and the pieces of adhesive material are generated from dicing of a semiconductor wafer, for example. These foreign matters may be deposited on the preciser 3. When the die pick-up mechanism 11 mounts the semiconductor chip 10 on the preciser 3 on which the foreign matters are piled, a load is accumulated at a portion of the semiconductor chip 10 making contact with the foreign matters. A crack may occur in the semiconductor chip 10 by the load being accumulated. A crack may occur in the semiconductor chip 10 as well by the load being accumulated at the portion making contact with the foreign matters upon when the die-bonding mechanism 15 picks up the semiconductor chip 10 from the preciser 3.

The detector 21 attached to the preciser 3 detects the elastic energy upon when the semiconductor chip 10 is mounted on the preciser 3, and upon when the semiconductor chip 10 is picked up from the preciser 3. The determining unit 7 determines the generation of a crack upon when the semiconductor chip 10 is mounted on the preciser 3, and upon when the semiconductor chip 10 is picked up from the preciser 3 in accordance with the detection results of the detector 21.

The preciser 3 is configured by using a metal member, for example, an aluminum material, a stainless steel material, and the like. Attenuation of a primary frequency component can be suppressed among the elastic waves propagated from the semiconductor chip 10 to the detector 21 by adapting the preciser 3 configured by using the metal member.

At a portion among the preciser 3 that propagates the elastic waves, members other than the metal member, for example, an elastic member and interface between the members are omitted as much as possible. By having a structure in which the members other than the metal member and the interface thereof are omitted, the preciser 3 can suppress the attenuation of the elastic waves. The detector 21 can accurately detect the elastic waves generated in the semiconductor chip 10 by suppressing the attenuation of the elastic waves propagated to the detector 21. Notably, the preciser 3 may be configured by using any of the members so long as it is possible to sufficiently detect the elastic waves generated in the semiconductor chip 10 by the detector 21.

Foreign matters derived from a driving system of the die-bonding device 2, and foreign matters derived from materials configuring a substrate, an adhesive layer, and the like may adhere to or be deposited on the die-bonding stage 17. When the die-bonding mechanism 15 mounts the semiconductor chip 10 on the object 16 on the die-bonding stage 17 on which the foreign matters are piled, a load is accumulated at a portion of the semiconductor chip 10. A crack may occur in the semiconductor chip 10 by the load being accumulated. Other than the above, in a case where a parallelism on the die-bonding stage 17 is not sufficiently secured, a crack may occur by biased load being applied to the semiconductor chip 10.

The detector 22 attached to the die-bonding stage 17 detects the elastic energy upon when the semiconductor chip 10 is mounted on the object 16. The determining unit 7 determines the generation of a crack upon when the semiconductor chip 10 is mounted on the object 16 in accordance with the detection result of the detector 22.

The die-bonding stage 17 is configured by using a metal member, for example, an aluminum material, a stainless steel material, and the like. Attenuation of a primary frequency component can be suppressed among the elastic waves propagated from the semiconductor chip 10 to the detector 22 by adapting the die-bonding stage 17 configured by using the metal member.

For example, the detector 22 is attached directly to the die-bonding stage 17. By making a distance from a position where the semiconductor chip 10 is to be mounted to the detector 22 as short as possible, the attenuation of the elastic waves in the propagation from the semiconductor chip 10 to the detector 22 can be suppressed.

At a portion among the die-bonding stage 17 that propagates the elastic waves, members other than the metal member, for example, an elastic member, and interface between the members, are omitted as much as possible. By having a structure in which the members other than the metal member and the interface thereof are omitted, the die-bonding stage 17 can suppress the attenuation of the elastic waves. The detector 22 can accurately detect the elastic waves generated in the semiconductor chip 10 by suppressing the attenuation of the elastic waves propagated to the detector 22.

Notably, the die-bonding stage 17 may be configured by using any of the members so long as it is possible to sufficiently detect the elastic waves generated in the semiconductor chip 10 by the detector 22. In the first embodiment, the detector 22 has heat resistance by which it can operate normally even when heat propagation from the heater 18 is received.

Figure 2:
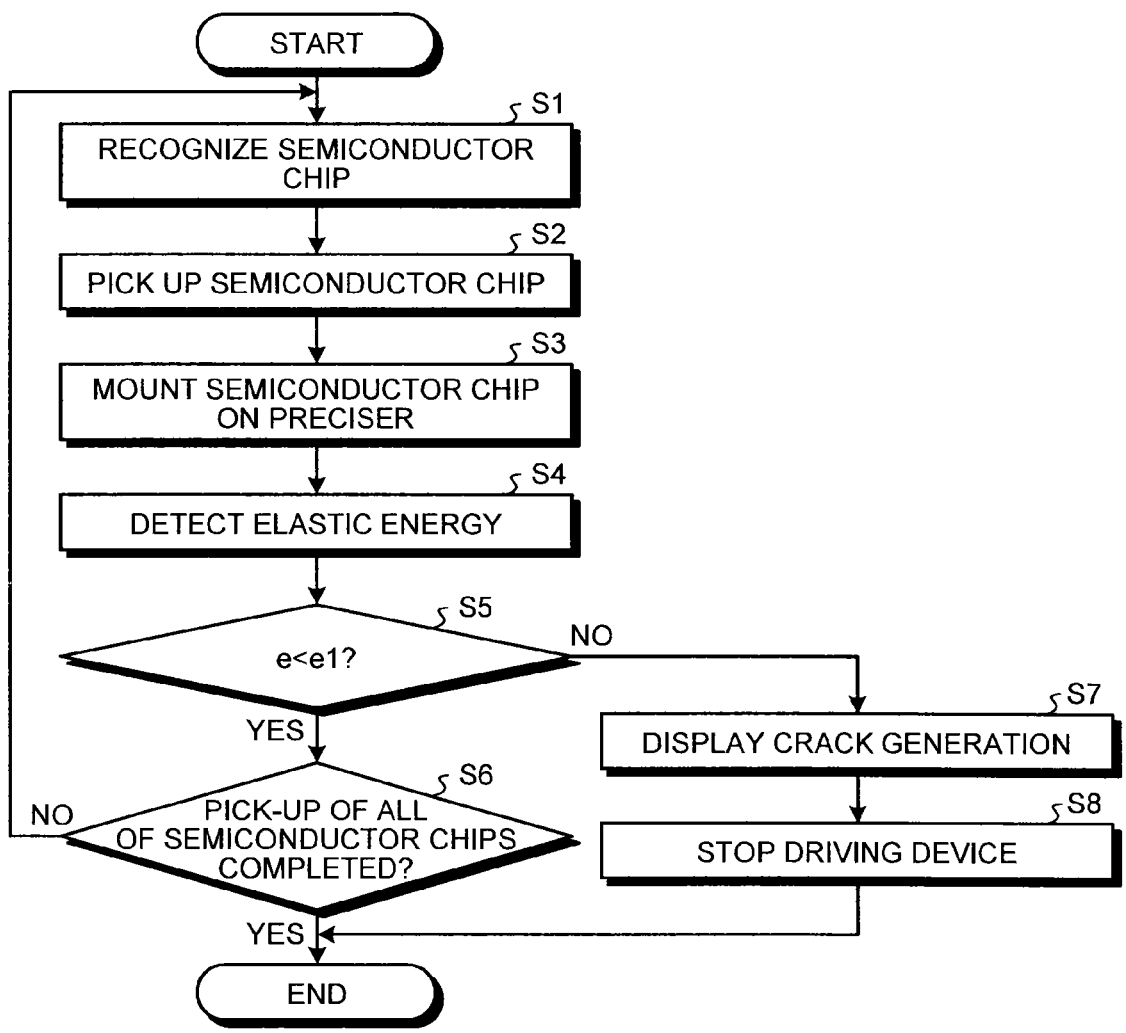
FIG. 2 is a flowchart illustrating an operation procedure of a pick-up device.

FIG. 2 is a flowchart illustrating an operation procedure of a pick-up device. The control device 4 identifies a semiconductor chip 10 to be the pick-up target of the pick-up device 1 by an ID that is identification information (step S1). The memory 6 stores the ID identified in step S1. The die pick-up mechanism 11 picks up the semiconductor chip 10 from the dicing sheet 13 in accordance with the control signal from the control device 4 (step S2).

The die pick-up mechanism 11 transfers the semiconductor chip 10 that had been picked up to the preciser 3 by a movement in the horizontal direction. The die pick-up mechanism 11 mounts the semiconductor chip 10 having been moved to the preciser 3 on the preciser 3 (step S3).

The detector 21 detects the elastic energy upon mounting the semiconductor chip 10 in step S3 (step S4). The detector 21 outputs the detection result of the elastic energy e to the control device 4. The memory 6 retains the detection result of the elastic energy e.

The memory 6 retains a predeterminedly set threshold e1. The threshold e1 is a threshold for determining the generation of a crack regarding the elastic energy detected by the detector 21. The determining unit 7 compares the elastic energy e detected in step S4 with the threshold e1 read out from the memory 6 (step S5).

In a case where the elastic energy e detected in step S4 is smaller than the threshold e1 (step S5, Yes), the determining unit 7 determines that no crack is generated in the semiconductor chip 10 with the ID identified in step S1. The preciser 3 performs a position correction on the semiconductor chip 10 which was determined as no crack being generated.

After the determination that no crack is being generated is made, the control device 4 determines whether or not the pick-up of all of the semiconductor chips 10 on the dicing sheet 13 has been completed (step S6). In a case where semiconductor chips 10 for which pick-up has not yet been completed still remain on the dicing sheet 13 (step S6, No), the control device 4 returns to step S1 and identifies an ID of a semiconductor chip 10 to be the next pick-up target of the pick-up device 1.

In a case where the pick-up of all of the semiconductor chips 10 on the dicing sheet 13 has been completed (step S6, Yes), the pick-up device 1 ends the pick-up operation on this dicing sheet 13.

On the other hand, in a case where the elastic energy e detected in step S4 is equal to or greater than the threshold e1 (step S5, No), the determining unit 7 determines that a crack is generated in the semiconductor chip 10 with the ID identified in step S1 by being mounted on the preciser 3. The determining unit 7 determines the generation of the crack by comparison with the threshold e1 that is to be the reference. The determining unit 7 outputs the determination result to the display device 5.

The display device 5 displays that the crack has occurred in accordance with the determination result of the determining unit 7 (step S7). The display device 5, for example, displays the ID of the semiconductor chip 10 in which the crack has occurred, and the message that the crack has occurred by mounting onto the preciser 3.

The control device 4 instructs to stop the drive of the pick-up device 1 in accordance with the determination result of the determining unit 7. The pick-up device 1 stops driving in accordance with the instruction from the control device 4 (step S8). The die pick-up mechanism 11 stops transferring the semiconductor chip 10 in accordance with the determination of the determining unit 7 that a crack has occurred. Due to this, the pick-up device 1 ends the pick-up operation.

Figure 3:
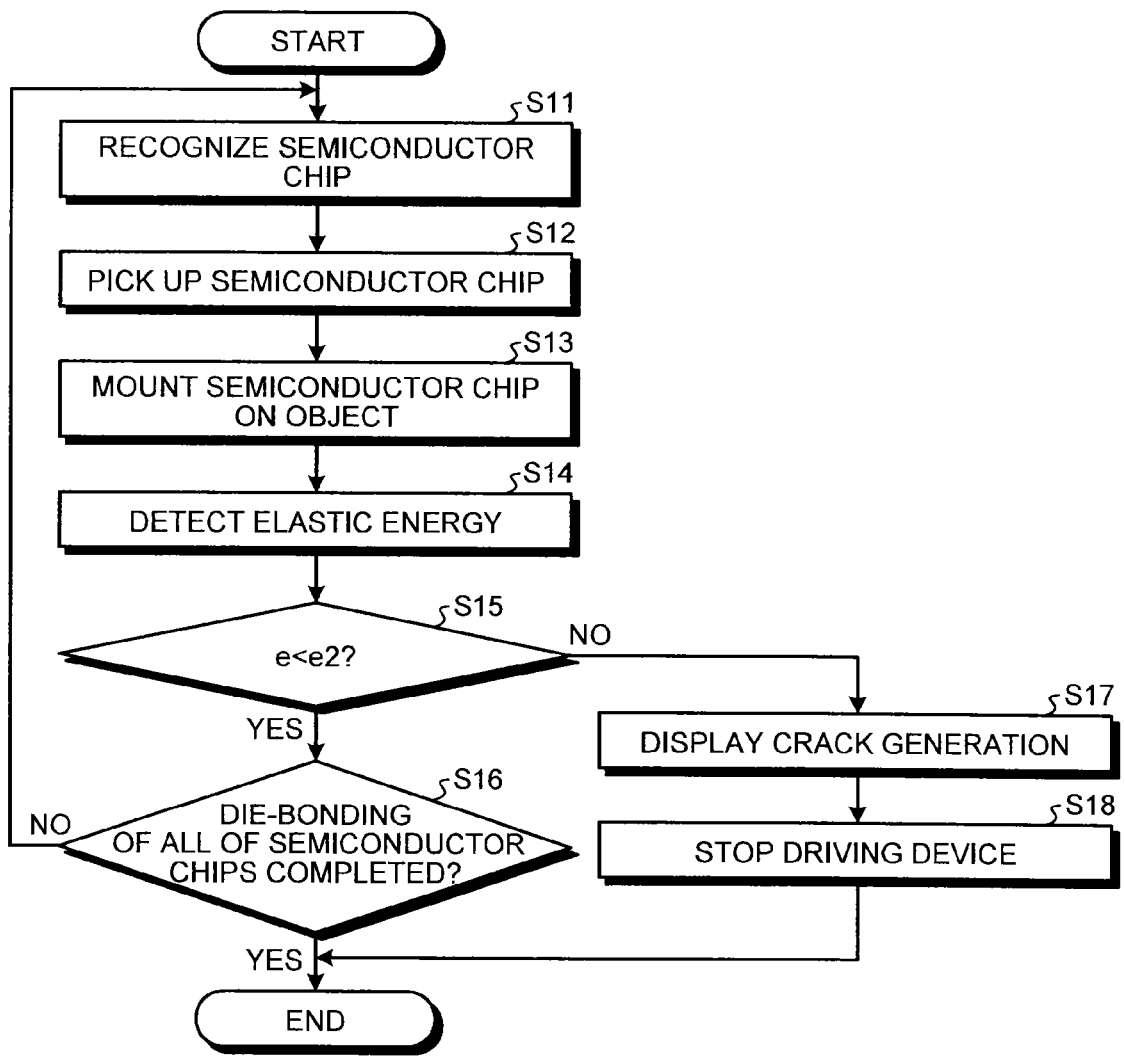
FIG. 3 is a flowchart illustrating an operation procedure of a die-bonding device.

FIG. 3 is a flowchart illustrating an operation procedure of a die-bonding device. The control device 4 identifies an ID of a semiconductor chip 10 to be the die-bonding target of the die-bonding device 2 (step S11). The memory 6 stores the ID identified in step S11. The die-bonding mechanism 15 picks up the semiconductor chip 10 from the preciser 3 in accordance with the control signal from the control device 4 (step S12).

The die-bonding mechanism 15 transfers the semiconductor chip 10 that has been picked up to the die-bonding stage 17 by the movement in the horizontal direction. The die-bonding mechanism 15 mounts the semiconductor chip 10 having been moved to the die-bonding stage 17 on the object 16, for example on a wiring substrate (step S13).

The detector 22 detects the elastic energy e upon mounting the semiconductor chip 10 in step S13 (step S14). The detector 22 outputs the detection result of the elastic energy e to the control device 4. The memory 6 retains the detection result of the elastic energy e.

The memory 6 retains a predeterminedly set threshold e2. The threshold e2 is a threshold for determining the generation of a crack regarding the elastic energy detected by the detector 22. The determining unit 7 compares the elastic energy e detected in step S14 with the threshold e2 read out from the memory 6 (step S15).

In a case where the elastic energy e detected in step S14 is smaller than the threshold e2 (step S15, Yes), the determining unit 7 determines that no crack is generated in the semiconductor chip 10 with the ID identified in step S1.

After the determination that no crack is being generated is made, the control device 4 determines whether or not the die-bonding of all of the semiconductor chips 10 to be passed on from the pick-up device 1 to the die-bonding device 2 has been completed (step S16). In a case where semiconductor chips 10 for which die-bonding has not yet been completed still remain (step S16, No), the control device 4 returns to step S11 and identifies an ID of a semiconductor chip 10 to be the next die-bonding target of the die-bonding device 2.

In a case where the die-bonding of all of the semiconductor chips 10 has been completed (step S16, Yes), the die-bonding device 2 ends the die-bonding operation.

On the other hand, in a case where the elastic energy e detected in step S14 is equal to or greater than the threshold e2 (step S15, No), the determining unit 7 determines that a crack is generated in the semiconductor chip 10 with the ID identified in step S11 by being mounted on the object 16. The determining unit 7 determines the generation of the crack by comparison with the threshold e2 that is to be the reference. The determining unit 7 outputs the determination result to the display device 5.

The display device 5 displays that the crack has occurred in accordance with the determination result of the determining unit 7 (step S17). The display device 5, for example, displays the ID of the semiconductor chip 10 in which the crack has occurred, and the message that the crack has occurred by mounting onto the object 16.

The control device 4 instructs to stop the drive of the die-bonding device 2 in accordance with the determination result of the determining unit 7. The die-bonding device 2 stops driving in accordance with the instruction from the control device 4 (step S18). The die bonding mechanism 15 stops transferring the semiconductor chip 10 in accordance with the determination of the determining unit 7 that a crack has occurred. Due to this, the die-bonding device 2 ends the die-bonding operation.

The semiconductor manufacturing device performs control in accordance with the determination of the generation of a crack and the determination result upon when the die-bonding mechanism 15 picks up the semiconductor chip 10 from the preciser 3 in step S12. Similar to step S4, the detector 21 detects the elastic energy e upon picking up the semiconductor chip 10 in step S12. Similar to step S5, the determining unit 7 compares the detected elastic energy e and the threshold e1.

In a case where the elastic energy e is smaller than the threshold e1, the determining unit 7 determines that no crack is generated in the semiconductor chip 10 that was picked up in step S12. The die-bonding device 2 performs the operations of step S13 and subsequent steps after the aforesaid determination.

On the other hand, in a case where the elastic energy e is equal to or greater than the threshold e1, the determining unit 7 determines that a crack was generated in the semiconductor chip 10 that was picked up in step S12. Similar to step S17, the display device 5 displays that the occurrence of the crack in accordance with the determination result of the determining unit 7. The control device 4 instructs to stop the drive of the die-bonding device 2 in accordance with the determination result of the determining unit 7. Similar to step S18, the die-bonding device 2 stops driving in accordance with the instruction from the control device 4.

According to the first embodiment, the semiconductor manufacturing device monitors the generation of a crack upon when the semiconductor chip 10 is mounted on the preciser 3 and upon when the semiconductor chip 10 is picked up from the preciser 3 by the detection of the elastic waves by the detector 21. The semiconductor manufacturing device monitors the generation of a crack upon when the semiconductor chip 10 is mounted on the object 16 by the detection of the elastic waves by the detector 22.

According to this, the semiconductor manufacturing device can detect the generation of a crack in the semiconductor chip 10 on a real time basis without using magnification observation and appearance inspection methods. When the generation of a crack is detected, the semiconductor manufacturing device stops the drive of the pick-up device 1 and the die-bonding device 2 to remove the semiconductor chip 10 in which the crack has occurred from the line without sending the semiconductor chip 10 to subsequent steps. The semiconductor manufacturing device can avoid mass production of a finished product that is to be a defective product. The semiconductor manufacturing device can improve yield.

Compared to the case where the defect of including the semiconductor chip 10 is determined upon inspection of the finished product, the burden of inspection of the finished product can be decreased by being able to remove the semiconductor chip 10 in which the crack has occurred at an early stage. Further, by reducing the finished product that is to be the defective product, wasting of components other than the semiconductor chip 10 in which the crack has occurred and manufacturing cost can be reduced.

A long time will be required from when the crack had actually occurred to the inspection of the finished product. Due to this, in the case of finding the cause in response to the inspection result, the identification of the cause may in some cases become difficult due to the replacement of an apparatus that had been the cause, or by replacement of a tool that had been the cause. According to the present embodiment, the semiconductor manufacturing device can avoid inconveniences as above caused by referring the defect by the generation of a crack on the inspection of the finished product.

The user can easily understand from the display of the display device 5 that the generation of a crack has taken place at the preciser 3 and the die-bonding stage 17. The user can understand the portion where the generation of a crack has taken place, whereby it becomes possible to easily and quickly verify the cause thereof. The semiconductor manufacturing device can suppress the number of staffs needed to find the cause of the generation of a crack and work burden therefor.

The semiconductor manufacturing device is not limited to those detecting the generation of a crack at both the preciser 3 and the die-bonding stage 17. The semiconductor manufacturing device will suffice so long as it can detect the generation of a crack at least in one of the preciser 3 and the die-bonding stage 17. The semiconductor manufacturing device only needs to include at least of the detectors 21, 22. By being provided with at least one of the detectors 21, 22, the semiconductor manufacturing device can detect the generation of a crack in the semiconductor chip 10 on the real time basis.

The pick-up device 1 and the die-bonding device 2 may include a marker that applies a mark to the semiconductor chip 10 determined as having the crack generation. Convenience can be increased, since the presence or absence of the generation of a crack can be confirmed by looking at the semiconductor chips 10.

Second Embodiment

Figure 4:
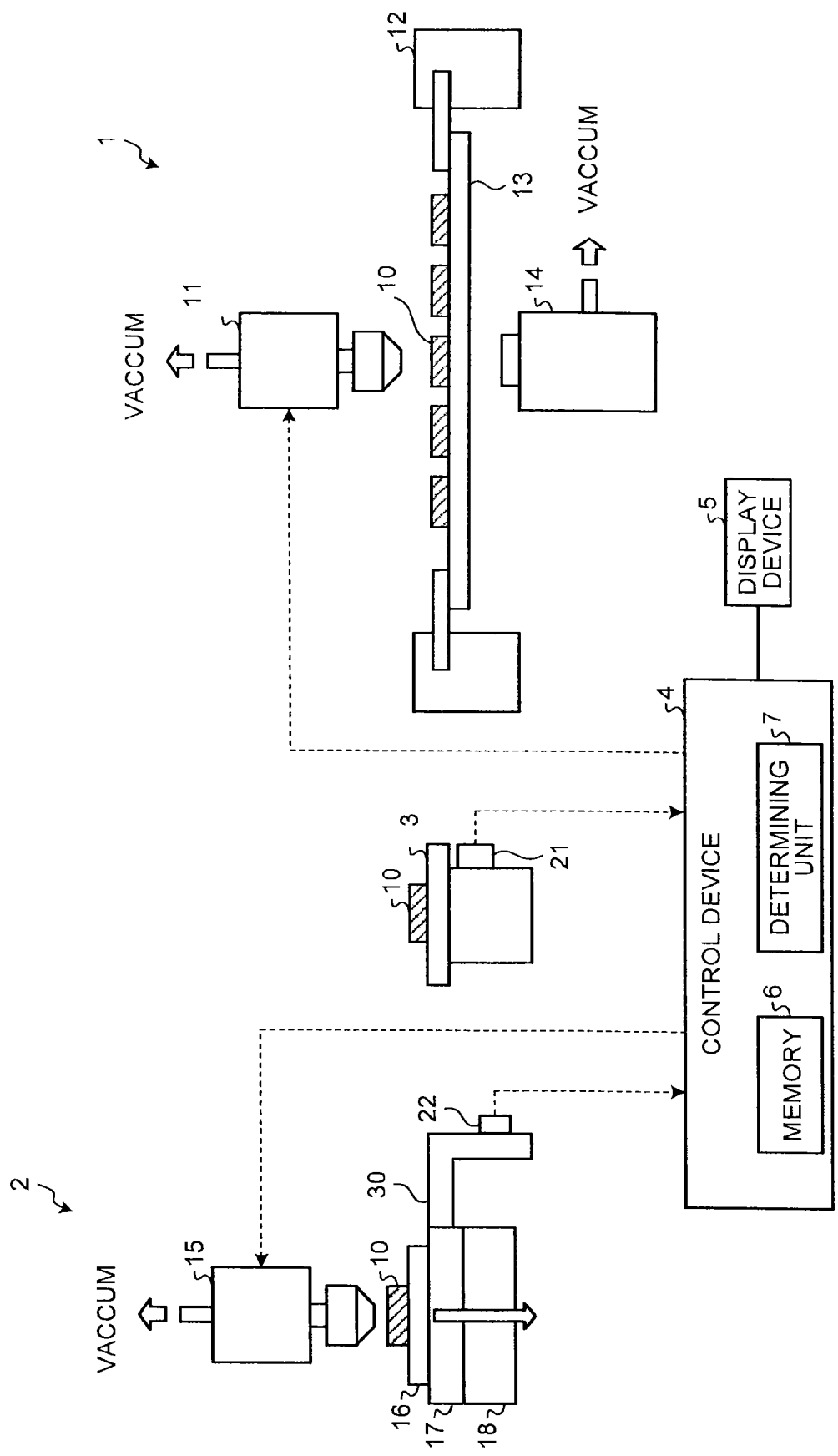
FIG. 4 is a diagram schematically illustrating a configuration of a semiconductor manufacturing device of a second embodiment.

FIG. 4 is a diagram schematically illustrating a configuration of a semiconductor manufacturing device of the second embodiment. Portions identical to the above first embodiment will be given the same signs, and overlapping descriptions will suitably be omitted.

A die-bonding stage 17 that is a second stage includes a heater 18 and a propagation plate 30. The propagation plate 30 that is propagating unit propagates elastic waves to a position separated from the heater 18 that is heating unit. A detector 22 is attached to the propagation plate 30.

The propagation plate 30 is configured by using a metal member, for example, such as an aluminum material, a stainless steel material, and the like. The propagation plate 30 has a bent shape in which one flat plate is bent in an L shape. One end of the propagation plate 30 is connected to a side surface at a portion other than the heater 18 among the die-bonding stage 17.

The detector 22 is arranged in the vicinity of an end portion on an opposite side from the side among the propagation plate 30 connected to the die-bonding stage 17. By being provided with the bent shape, the propagation plate 30 configures an opened portion between a portion where the detector 22 is provided and the heater 18. This opened portion suppresses heat propagation from the heater 18 to the detector 22, and enhances heat diffusion from the propagation plate 30.

The die-bonding stage 17 may be provided with a layer formed of a heat insulating member such as a ceramic and the like at the opened portion. Due to this, the die-bonding stage 17 can shut off the heat propagation from the heater 18 to the detector 22 by using this layer.

The die-bonding stage 17 can suppress attenuation of a primary frequency component among the elastic waves propagated from a semiconductor chip 10 to the detector 22 by adapting the propagation plate 30 configured by using the metal member.

The die-bonding stage 17 can suppress the attenuation of the elastic waves propagated to the detector 22 by having a structure in which a portion to propagate the elastic waves omits members other than the metal member, for example, a portion formed of an elastic member, and interface between the members, as much as possible. The detector 22 can accurately detect the elastic waves generated in the semiconductor chip 10 by suppressing the attenuation of the elastic waves propagated to the detector 22.

Notably, the propagation plate 30 may be configured by using any of the members so long as it is possible to sufficiently detect the elastic waves generated in the semiconductor chip 10 by the detector 22. The propagation plate 30 only needs to be able to propagate the elastic waves to a position separated from the heater 18, and its shape, and arranged position may be arbitrary.

By providing the propagation plate 30, the die-bonding stage 17 arranges the detector 22 at the position separated from the heater 18. The propagation plate 30 diffuses heat from the heater 18. The die-bonding stage 17 can propagate the elastic waves to the detector 22 and suppress the heat propagation to the detector 22 by the propagation plate 30. The propagation plate 30 may suitably set a size of the opened portion in accordance with thermal influence on the detector 22.

According to the second embodiment, the semiconductor manufacturing device can adapt the detector 22 even if it does not have heat resistance of being able to endure use under a high temperature environment of 100° C. or more, for example. The detector 22 can adapt conditions other than heat resistance, for example, that places weight to price, detection sensitivity, and the like.

In the second embodiment also, the semiconductor manufacturing device can detect the generation of a crack in the semiconductor chips 10 on a real time basis, similar to the first embodiment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A semiconductor manufacturing device comprising:
    a first stage on which a semiconductor chip is mounted, and that corrects a position of the semiconductor chip;
    a second stage that supports an object into which the semiconductor chip is to be installed;
    a transfer unit configured to transfer the semiconductor chip picked up from the first stage to the second stage, and mounting the semiconductor chip on the object; and a detector attached to at least one of the first stage and the second stage, that detects an elastic wave from the semiconductor chip.

2. The semiconductor manufacturing device according to claim 1, further comprising:
a determining unit configured to determine generation of a crack in the semiconductor chip in accordance with a detection result of the elastic waves by the detector.

3. The semiconductor manufacturing device according to claim 2, wherein
the determining unit determines as that the crack has occurred in a case where energy of the detected elastic wave exceeds a predeterminedly set threshold.

4. The semiconductor manufacturing device according to claim 2, further comprising:
a display unit configured to display a determination result by the determining unit.

5. The semiconductor manufacturing device according to claim 1, wherein
the detector is attached to the first stage, and detects energy of the elastic wave when the semiconductor chip is mounted on the first stage, and energy of the elastic wave when the semiconductor chip is picked up from the first stage.

6. The semiconductor manufacturing device according to claim 1, wherein
the detector is attached to the first stage, and
the first stage is configured by using a metal member.

7. The semiconductor manufacturing device according to claim 1, wherein
the detector is attached to the second stage, and detects energy of the elastic wave when the semiconductor chip is mounted on the object.

8. The semiconductor manufacturing device according to claim 1, wherein
the detector is attached to the second stage, and
the second stage is configured by using a metal member.

9. The semiconductor manufacturing device according to claim 1, wherein
the second stage includes
a heating unit configured to heat the object and
a propagating member that propagates the elastic wave to a position separated from the heating unit, and
the detector is attached to the propagating member.

10. The semiconductor manufacturing device according to claim 9, wherein
the propagating member is configured by using a metal member.

11. The semiconductor manufacturing device according to claim 1, wherein
the detector includes a filter that removes noise upon detecting energy of the elastic wave.

12. A semiconductor manufacturing method comprising:
correcting a position of a semiconductor chip mounted on a first stage;
picking up the semiconductor chip from the first stage;
transferring the semiconductor chip to a second stage supporting an object into which the semiconductor chip is to be installed;
mounting the semiconductor chip on the object;
detecting an elastic wave of the semiconductor chip at least at one of the first stage and the second stage; and
determining generation of a crack in the semiconductor chip in accordance with a detection result of the elastic wave.

13. The semiconductor manufacturing method according to claim 12, wherein
the semiconductor chip that was separated and transferred to the first stage is mounted on the first stage.

14. The semiconductor manufacturing method according to claim 13, wherein
in a case where a determination is made that the crack has occurred in accordance with the detection result of the elastic wave at the first stage, the transfer of the semiconductor chip to the first stage is stopped.

15. The semiconductor manufacturing method according to claim 12, wherein
in a case where a determination is made that the crack has occurred in accordance with the detection result of the elastic wave at the second stage, the transfer of the semiconductor chip from the first stage to the second stage is stopped.

16. The semiconductor manufacturing method according to claim 12, wherein
a determination is made that the crack has occurred in a case where energy of the detected elastic wave exceeds a predeterminedly set threshold.

17. The semiconductor manufacturing method according to claim 12, further comprising:
displaying a result of determining the generation of a crack.

18. The semiconductor manufacturing method according to claim 12, wherein
at the second stage, the elastic wave that had propagated through a propagating member attached to the second stage is detected.

* * * * *